United States Patent [19]
Phillips

[11] Patent Number: 5,383,879
[45] Date of Patent: Jan. 24, 1995

[54] BONE WAX APPLICATOR AND METHOD FOR DRESSING BONE TISSUE

[76] Inventor: Arnold G. Phillips, 1420 Madison Dr., Buffalo Grove, Ill. 60089

[21] Appl. No.: 915,806
[22] PCT Filed: Jan. 22, 1990
[86] PCT No.: PCT/US90/00479
§ 371 Date: Jan. 15, 1993
§ 102(e) Date: Jan. 15, 1993

[51] Int. Cl.6 .................................. A61B 17/56
[52] U.S. Cl. ............................ 606/86; 604/309
[58] Field of Search ................ 606/86, 92, 93; 604/289, 293, 290, 304, 309

[56] References Cited
U.S. PATENT DOCUMENTS

| 737,066 | 8/1903 | Bonar. |
| 932,388 | 8/1909 | Hartsock. |
| 1,852,114 | 4/1932 | Green. |
| 2,057,500 | 10/1936 | O'Connor. |
| 3,396,419 | 8/1968 | Richter et al.. |
| 4,308,633 | 1/1982 | Van Huffel et al. ............ 15/104.93 |

FOREIGN PATENT DOCUMENTS

| 1265013 | 1/1990 | Canada .................................. 606/86 |
| 2834801 | 2/1980 | Germany. |
| 862949 | 9/1981 | U.S.S.R. ............................... 604/290 |

Primary Examiner—Tamara L. Graysay
Attorney, Agent, or Firm—Merchant, Gould, Smith, Welter & Schmidt

[57] ABSTRACT

An applicator for-applying bone wax to bone tissue in which a layer of bone wax covers selected surface portions of a pattie of surgical fibre, and a method of applying bone wax from an applicator having a layer of bone wax covering portions of a pattie wherein the bone wax layer is drawn across the bone to deposit the bone wax, and the deposited bone wax is then molded over the bone tissue with exposed portions of the applicator pattie.

8 Claims, 3 Drawing Sheets

BONE WAX APPLICATOR AND METHOD FOR DRESSING BONE TISSUE

BACKGROUND OF THE INVENTION

1. Field of the Invention

The present invention is related to surgery and surgical procedures and, more specifically, to surgery involving cutting of bone tissue, such as orthopedic, cardiac, and neurological surgery, wherein bleeding of bone tissue is to be stopped.

2. Description of the Prior Art

Various medical, veterinary, and dental surgical procedures involve the cutting of bone tissue during the operation. Examples of such procedures are laminectomies, craniotomies, and cardiac surgery procedures involving splitting of the sternum. Typically, the bone tissue is cut with a rongeur or a saw.

As with other living tissue, bone tissue of animals and humans bleeds when it is cut. Accordingly, a means for stopping the bleeding is required. For many years, compositions generally known as bone wax have been used to dress the bone tissue and retard its bleeding. While bone wax compositions have been found that are effective, no devices or surgical procedures have been developed so that the bone wax can be effectively and conveniently applied to the bleeding bone tissue.

Typically, surgical bone wax is sold in sterile packages that are opened at the time when the bone wax is to be applied. The bone wax is applied to the tissue in various ways. Some surgeons shape an amount of bone wax into a suitable form such as a ball and press it into the tissue either with their gloved hand or a suitable surgical instrument. When the bone wax is applied in this manner, it must then be distributed over the entire surface where the bone tissue has been cut to dress the bleeding tissue. If this is done with a surgical instrument, an incomplete distribution of bone wax sometimes results. The bone wax can be better distributed, if the surgeon uses his gloved hand to smooth the bone wax over the bleeding bone tissue. However, the surgeon risks contamination of the operative field if he should tear or puncture his glove on the exposed bone, and risks infection of his hand as well if it is punctured by a bone spicule. Accordingly, many surgeons have used surgical patties to distribute the bone wax over the bone tissue.

Disadvantages and difficulties have appeared with all these prior art devices and techniques. The package in which the bone wax is provided is small and somewhat awkward to open in a sterile operative field. Moreover, each application of bone wax required at least two steps in the surgical procedure. In a typical orthopedic or neurosurgical operation in which bone wax is used, as many as several dozen separate applications of bone wax may be made. Therefore, the additional steps for applying bone wax consume a considerable portion of the time necessary for the operation. For example, in a neurosurgical operation requiring four hours, as much as 10 to 30 minutes may be spent in merely applying bone wax. Accordingly, a device and method for applying bone wax more efficiently and effectively would benefit the patient by lowering his exposure to possible sources of contamination, and by reducing the time that he would be under anesthesia.

SUMMARY OF THE INVENTION

The presently disclosed invention includes an applicator for applying bone wax to bleeding bone tissue, the applicator comprising a reinforcement layer of pliable surgical fiber having a layer of bone wax covering at least a portion thereof.

Preferably, the bone wax layer is disposed on one end of a surgical reinforcement layer comprised of a cotton or cotton-like material. The applicator may be further provided with identification means, including x-ray detectable strips, for physically or radiologically locating the applicator both during and after the operation.

Also preferably, the bone wax applicator is packaged in a sterile package that can be readily opened onto the surgical field.

The presently disclosed invention further includes a surgical method for dressing bleeding bone tissue with bone wax in which a bone wax layer located on a surgical fiber reinforcement layer is placed against the bone tissue and then drawn across the bone tissue such that a portion of the bone wax is deposited on the bone tissue. The deposited bone wax is then molded over the entire portion of bleeding bone tissue with an exposed surface of the reinforcement layer.

Other details, objects and advantages of the invention will become apparent as the following description of the preferred embodiment of the invention and the preferred method of practicing the same proceeds.

PREFERRED EMBODIMENT OF THE INVENTION

Figure 1:
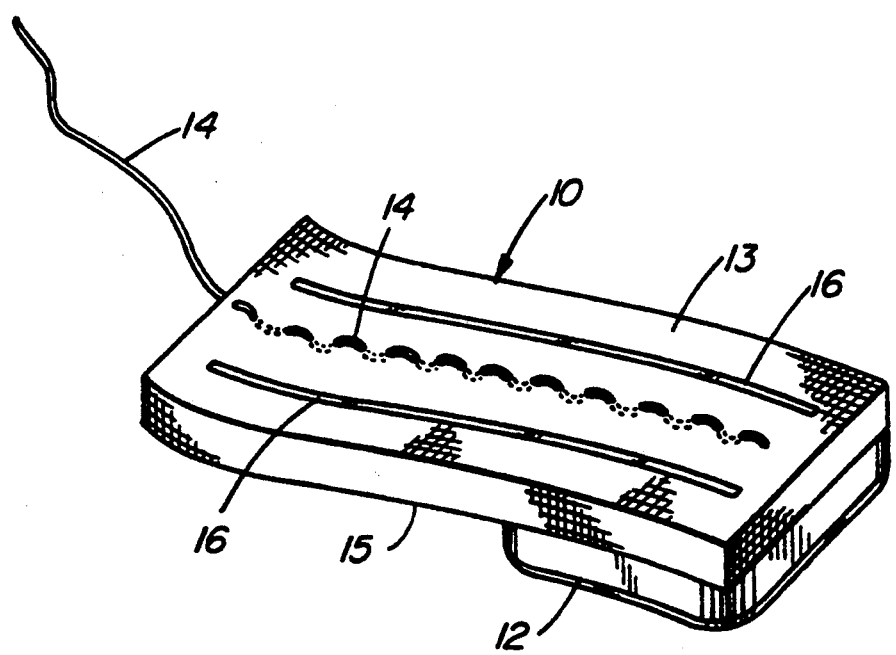
FIG. 1 shows a perspective view of the bottom side of the preferred embodiment of the invention.
Figure 2:
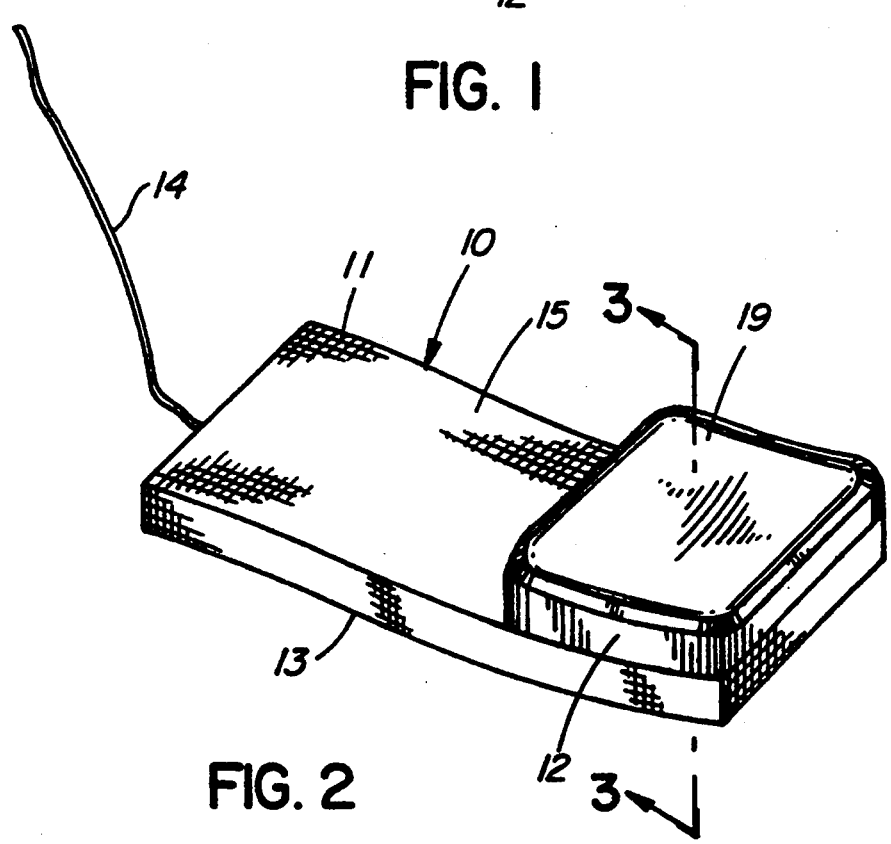
FIG. 2 shows another perspective view of the embodiment of FIG. 1.

As shown in FIGS. 1 and 2, the presently preferred bone wax applicator includes a reinforcement layer 10 of surgical fiber or surgical gauze. The surgical fiber can be a natural fiber, such as cotton, or a synthetic fiber, such as rayon, of a combination of natural and synthetic fibers. The term fiber, as herewith used, includes random unwoven fibers and oriented fibers, and in particular includes woven fibers such as gauze. Preferably, layer 10 could be a surgical reinforcement layer and/or layers. While reinforcement layer 10 as shown in FIGS. 1 and 2, is generally rectangular, it could also have a square or other shape.

Covering a portion of a major surface of reinforcement layer 10 is a layer 12 of bone wax. Bone wax layer 12 can be comprised of any natural or synthetic composition that has accepted usage as bone wax. One example of such a natural composition is Horseley's wax which includes seven parts of beeswax to one part each of almond oil and salicylic acid. While bone wax layer 12 can be otherwise disposed on reinforcement layer 10, it is preferred that bone wax 12 be located at one end thereof for the reason that is believed to be easier to apply the bone wax to bleeding bone tissue with this arrangement. Alternatively, however, as for example where reinforcement layer 10 is sufficiently small that an adequate amount of bone wax would not be otherwise carried on the reinforcement layer, bone wax layer 12 can be made to cover an entire major surface of reinforcement layer 10. Surfaces of reinforcement layer 10 that are not covered by bone wax layer 12 are hereafter referred to as exposed surfaces.

Preferably, the applicator includes an identification string 14 that can be used as an aid in physically locating the applicator when it is used on bone tissue exposed by an incision closeable with a suture. Identification string 14 can be comprised of silk or other suitable material. Also preferably included are X-ray strips 16 that are detectable by radiological examination and would be useful in detecting an applicator inside the patient after the operation is completed.

The applicator is kept in sterile condition in a suitable package. Upon opening the package onto the operation field, the applicator is ready for immediate use without preliminary preparation.

In accordance with the use of the presently disclosed applicator, the applicator is placed against the bleeding bone tissue such that bone wax layer 12 is in contact with the bone tissue. The applicator is then drawn tangentially across the bone surface such that bone wax is abraded from layer 12 and becomes deposited on the bone tissue. The surgeon then dresses the bone wax over uncovered areas of bone tissue by spreading the deposited bone wax with exposed portions of reinforcement layer 10.

Figure 3:
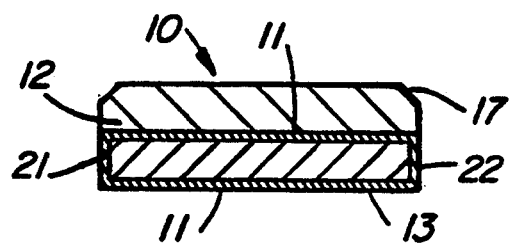
FIG. 3 shows a cross sectional view along line 3—3 of FIG. 2.

As shown in FIG. 3 which illustrates a preferred embodiment of the invention, reinforcement layer 10 includes a layer of fabric 11 on upper and lower surfaces, 13 and 15 respectively, the four edges of the bone wax 12 adjacent the reinforcement layer 10 may be beveled in order to aid in the elimination of stray pieces of bone wax and/or fabric from breaking off from the applicator. The fraying of the bone wax and fabric is aseptic and is thus undesirable. Furthermore the bone wax may be heat-sealed onto the fabric 15. Through heat sealing, the bone wax 12 is bonded more securely to the fabric 15 thereby allowing the user to apply more pressure to the bone wax during application of the wax, over rough-edged bleeding bone tissue.

Figure 4:
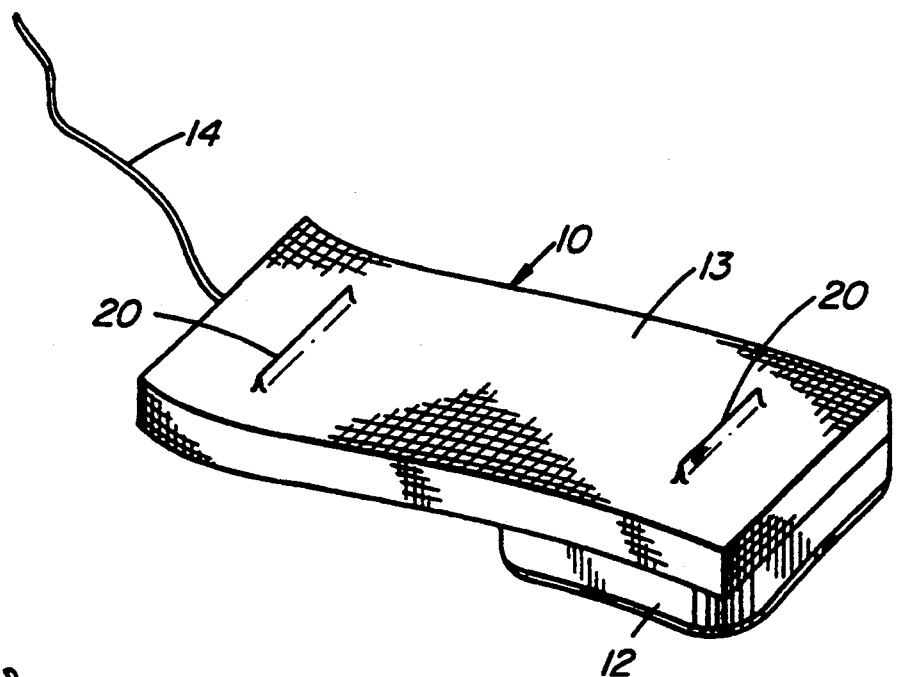
FIG. 4 shows a perspective view of the bottom side of another preferred embodiment of the invention.

In a further embodiment of the present invention, as illustrated in FIG. 4, it may also be desirable to include one or more longitudinal elevations of fabric or creases 20, on the upper surface 13 of the reinforcement layer 10 to provide means for the user to grip the reinforcement layer with a surgical instrument, such as forceps, if manipulation of the reinforcement layer with the aid of a surgical instrument is required. The longitudinal elevations of fabric or creases 20 may be oriented variously (vertically, horizontally or diagonally) and may be located at various positions about the upper surface 13 of the reinforcement layer 10 depending on the requirements of the user. FIG. 4 illustrates one such arrangement.

Figure 5:
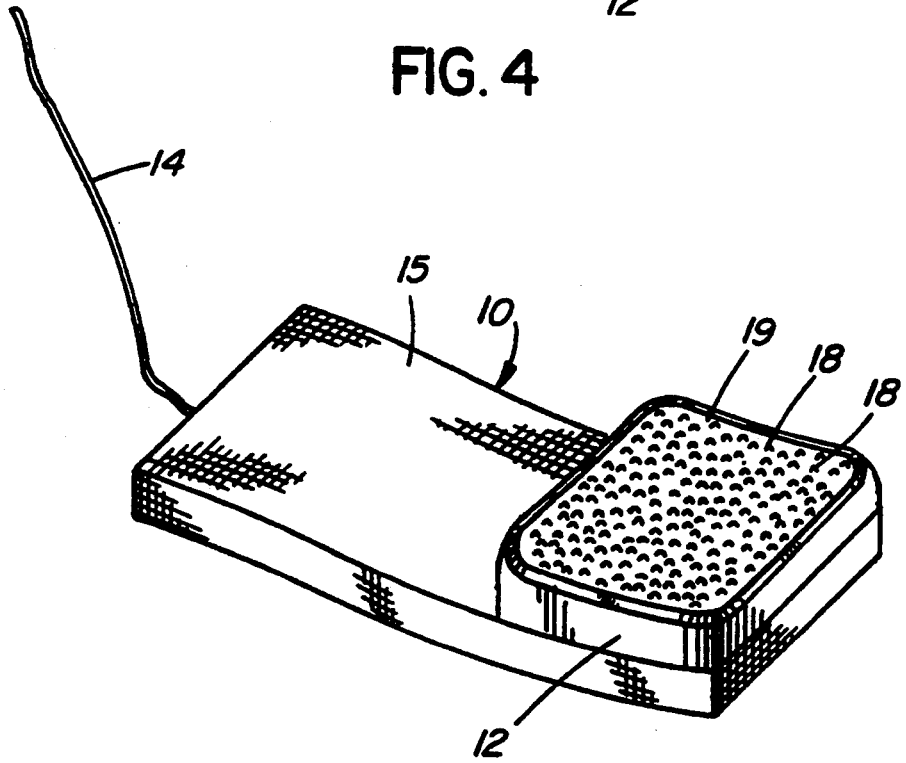
FIG. 5 shows a perspective view of the top side of yet another preferred embodiment of the present invention wherein the surface of the bone wax is stippled.
Figure 6A:
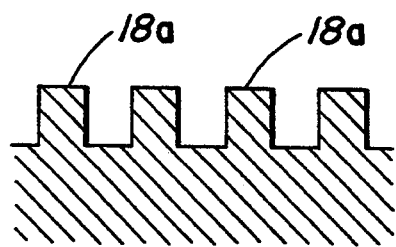
FIGS. 6A–E illustrate cross-sectional views of the stippling of the embodiment shown in FIG. 5.
Figure 6B:
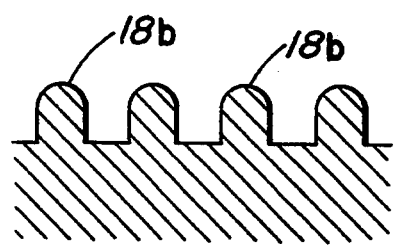
Figure 6C:
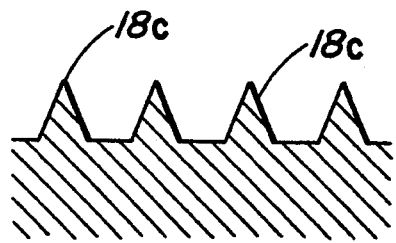
Figure 6D:
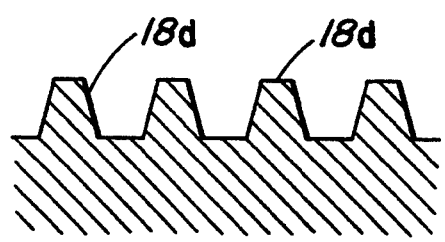
Figure 6E:
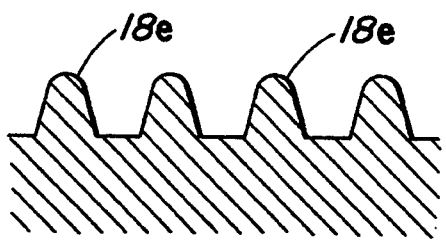

If desirable, the applicator or free surface 19 of the reinforcement layer may be smooth as shown in FIG. 2 or may be stippled i.e. having multiple raised surfaces 18 distributed throughout the free surface 19, as shown in FIG. 5. The purposes of providing a stippled surface is for greater exposure, of volume with respect to surface area, of bone wax to bleeding bone tissue and to provide increased gripping or catching power of the bone wax during application. It is understood that the shape of the raised surfaces 18a, 18b, 18c, 18d, and 18e may be variable as shown in FIGS. 6A-E, respectively, and the distribution of the "stippling" may be uniform or nonuniform although uniform distribution is preferable as is illustrated generally in FIG. 5.

While a presently preferred embodiment of the invention has been shown and described, and a presently preferred method of practicing the same has been illustrated, it is to be understood that the invention is not limited thereto but may be otherwise variously embodied and practiced within the scope of the following claims.

The embodiments of the invention in which an exclusive property or privilege is claimed are defined as follows:

1. An applicator for applying bone wax to bleeding bone tissue exposed by an incision closeable with a suture, said applicator comprising:
   a reinforcement layer of pliable, surgical fiber;
   a layer of bone wax that covers one end of a major surface of the reinforcement layer, such that said bone wax can be applied to the bone tissue by scraping the bone wax layer against the tissue; and
   an identification string attached to said reinforcement layer for aiding in physically locating the applicator for removal before closure with the suture.

2. The applicator of claim 1 further comprising:
   an x-ray detectable string attached to said reinforcement layer for revealing the presence of the reinforcement layer upon radiological examination.

3. The applicator of claim 1 wherein said surgical fiber is comprised of a cotton material.

4. The applicator of claim 1 wherein said reinforcement layer is comprised of surgical gauze.

5. The applicator of claim 1 wherein said layer of bone wax includes an applicator surface which is smooth.

6. An applicator for applying bone wax to bleeding bone tissue, said applicator comprising:
   a reinforcement layer of pliable, surgical fiber; and
   a layer of bone wax that covers one end of a major surface of the reinforcement layer, such that said bone wax can be applied to the bone tissue by scraping the bone wax layer against the tissue, said layer of bone wax including a surface with edges and a bevel on said edges.

7. An applicator for applying bone wax to bleeding bone tissue, said applicator comprising:
   a reinforcement layer of pliable, surgical fiber, said reinforcement layer including an outer layer of fabric having an elevation therein to provide means to manipulate the applicator with a surgical instrument; and
   a layer of bone wax that covers one end of a major surface of the reinforcement layer, such that said bone wax can be applied to the bone tissue by scraping the bone wax layer against the tissue.

8. An applicator for applying bone wax to bleeding bone tissue, said applicator comprising:
   a reinforcement layer of pliable, surgical fiber; and
   a layer of bone wax that covers one end of a major surface of the reinforcement layer, such that said bone wax can be applied to the bone tissue by scraping the bone wax layer against the tissue, said layer of bone wax including a surface which is stippled in the form of raised points.

* * * * *